United States Patent
Safai et al.

(10) Patent No.: US 7,925,452 B2
(45) Date of Patent: Apr. 12, 2011

(54) METHOD AND APPARATUS FOR NONDESTRUCTIVE CORROSION DETECTION USING QUANTUM DOTS

(75) Inventors: Morteza Safai, Seattle, WA (US); Gary Georgeson, Federal Way, WA (US)

(73) Assignee: The Boeing Company, Chicago, IL (US)

( * ) Notice: Subject to any disclaimer, the term of this patent is extended or adjusted under 35 U.S.C. 154(b) by 231 days.

(21) Appl. No.: 11/763,979

(22) Filed: Jun. 15, 2007

(65) Prior Publication Data

US 2008/0312847 A1 Dec. 18, 2008

(51) Int. Cl.
*G01B 15/06* (2006.01)
(52) U.S. Cl. ............ 702/34; 702/35; 702/40; 702/66
(58) Field of Classification Search ............ 702/19, 702/21, 23, 28, 40, 95, 179, 180, 182, 183; 252/500; 257/14, 29, 76; 427/67
See application file for complete search history.

(56) References Cited

U.S. PATENT DOCUMENTS

| | | | |
|---|---|---|---|
| 5,482,890 A | 1/1996 | Liu et al. | |
| 6,379,622 B1 | 4/2002 | Polak et al. | |
| 6,627,914 B1 * | 9/2003 | Komiyama et al. | 257/29 |
| 6,657,232 B2 * | 12/2003 | Morkoc | 257/76 |
| 6,717,664 B2 | 4/2004 | Floyd et al. | |
| 7,002,079 B2 | 2/2006 | Mitchell et al. | |
| 7,005,669 B1 | 2/2006 | Lee | |
| 7,342,235 B1 | 3/2008 | Harrison et al. | |
| 7,528,372 B2 | 5/2009 | Garvey et al. | |
| 2003/0160182 A1 | 8/2003 | Petrich et al. | |
| 2004/0211894 A1 | 10/2004 | Hother et al. | |
| 2004/0241424 A1 | 12/2004 | Barbera-Guillem | |
| 2004/0256612 A1 * | 12/2004 | Mohseni et al. | 257/14 |
| 2006/0152706 A1 | 7/2006 | Butland | |
| 2007/0048867 A1 | 3/2007 | Farmer | |
| 2007/0194297 A1 * | 8/2007 | McCarthy et al. | 257/14 |
| 2008/0050513 A1 * | 2/2008 | Wang et al. | 427/67 |

FOREIGN PATENT DOCUMENTS

| | | | |
|---|---|---|---|
| WO | 2005124340 A1 | 12/2005 | |
| WO | 2006107331 A1 | 10/2006 | |
| WO | 2006107493 A1 | 10/2006 | |

OTHER PUBLICATIONS

U.S. Appl. No. 12/335,724, filed Dec. 16, 2008, Davis et al.
U.S. Appl. No. 12/390,965, filed Feb. 23, 2009, Safai et al.
USPTO office action for application U.S. Appl. No. 12/390,965, dated Aug. 20, 2010.
Bakkers et al., Excited-State Dynamics in CdS Quantum Dots Absorbed on a Metal Electrode, J Phys Chem B, vol. 103, No. 14, 1999, pp. 2781-2788.
"Making Nanodots Useful For Chemistry" Jun. 19, 2003, 1 page http://www.sciencedaily.com/releases/2003/06/030619075658.htm.

* cited by examiner

*Primary Examiner* — Eliseo Ramos Feliciano
*Assistant Examiner* — Felix E Suarez
(74) *Attorney, Agent, or Firm* — Yee & Associates, P.C.; Kathryn A. Soucy

(57) ABSTRACT

A method, apparatus, and computer usable program code for non-destructive detection of corrosion using quantum dots. In one embodiment, a surface of an area on a commodity associated with a set of quantum dots is tested. A pattern of wavelengths emitted by the set of quantum dots associated with the surface of the commodity is detected to form a quantum dot pattern. The quantum dot pattern is analyzed to determine whether corrosion has occurred in the area on the surface of the commodity.

17 Claims, 6 Drawing Sheets

METHOD AND APPARATUS FOR NONDESTRUCTIVE CORROSION DETECTION USING QUANTUM DOTS

BACKGROUND

1. Field

The disclosure is related generally to quantum dots and in particular to a method and apparatus for nondestructive inspection of structures. More particularly, the disclosure is directed to a method, apparatus, and computer usable program code for enhancing detection of corrosion on a surface of a structure by detecting quantum dots associated with the surface.

2. Background

During the manufacture, maintenance, and/or rework of many commodities, such as aircraft commodities, it can be extremely important to ensure that external and/or internal surfaces of the commodity do not have any corrosion.

Therefore, detection of corrosion may be very important. However, corrosion on a surface may be hidden or masked underneath layers of paint or other surface coatings. Destructive means of corrosion detection require the stripping or removal of paint and/or disassembly of parts and assemblies to identify corrosion. These processes are destructive, slow, inefficient, and may be cost prohibitive.

Currently available nondestructive corrosion inspection (NDI) is generally performed visually, using electromagnetic inspection, eddy current or ultrasonic inspection methods, which can measure metal thinning due to corrosion. However, these approaches require more inspections and disassemblies than would otherwise be required for a very early detection and monitoring capability. In addition, visual inspections require a technician or other maintenance personnel to visually inspect all surfaces for signs and evidence of corrosion, such as visible rust. This can be a time consuming, expensive, and unreliable process.

In addition, corrosion is often very difficult to detect under paint or other coatings, in remote areas, and/or in difficult to reach areas. For remote or limited access areas, visual inspection may be made possible through borescopes. Interpretation may frequently be difficult and sensitivity to corrosion may be limited with this approach because corrosion may appear similar to dirt, paint chips, or other foreign material.

Moreover, maintenance personnel and corrosion inspectors must wait until corrosion on a surface is substantial enough to be detected visually. By the time the corrosion is detected by these means, the corrosion may have resulted in greater damage to the commodity, and a correspondingly higher cost of rework, than if the corrosion had been detected at an earlier time.

Therefore, it would be advantageous to have an improved method, apparatus, and computer usable program code for non-destructive corrosion detection.

SUMMARY

An embodiment of the disclosure provides a method, apparatus, and computer usable program code for non-destructive detection of corrosion using quantum dots. A surface of a commodity associated with a set of quantum dots is tested to form a test area. A pattern of wavelengths emitted by the set of quantum dots associated with the test area is detected to form a quantum dot pattern. The quantum dot pattern is analyzed to determine whether corrosion has occurred in the test area of the commodity.

Another advantageous embodiment provides a system for non-destructive detection of corrosion using quantum dots. The system includes a commodity; a set of quantum dots associated with an area of the commodity to form a test area; and a quantum dot detector, wherein the quantum dot detector detects a pattern of wavelengths emitted by the set of quantum dots associated with the test area of the commodity to form a quantum dot pattern; and analyzes the quantum dot pattern to determine whether corrosion has occurred in the test area of the commodity.

In another illustrative embodiment, a computer program product having a computer usable medium including computer usable program code for non-destructive detection of corrosion using quantum dots is provided. The computer program product comprises computer usable program code for detecting a pattern of wavelengths emitted by the set of quantum dots associated with the surface of the commodity to form a quantum dot pattern in response to a test of a surface of an area on a commodity associated with a set of quantum dots to form a test area; and computer usable program code for analyzing the quantum dot pattern to determine whether corrosion has occurred in the test area of the commodity.

The features, functions, and advantages can be achieved independently in various embodiments of the disclosure or may be combined in yet other embodiments in which further details can be seen with reference to the following description and drawings.

BRIEF DESCRIPTION

The novel features believed characteristic of the invention are set forth in the appended claims. The invention itself, however, as well as a preferred mode of use, further objectives and advantages thereof, will best be understood by reference to the following detailed description of an advantageous embodiment of the disclosure when read in conjunction with the accompanying drawings, wherein:

DESCRIPTION

Figure 1:
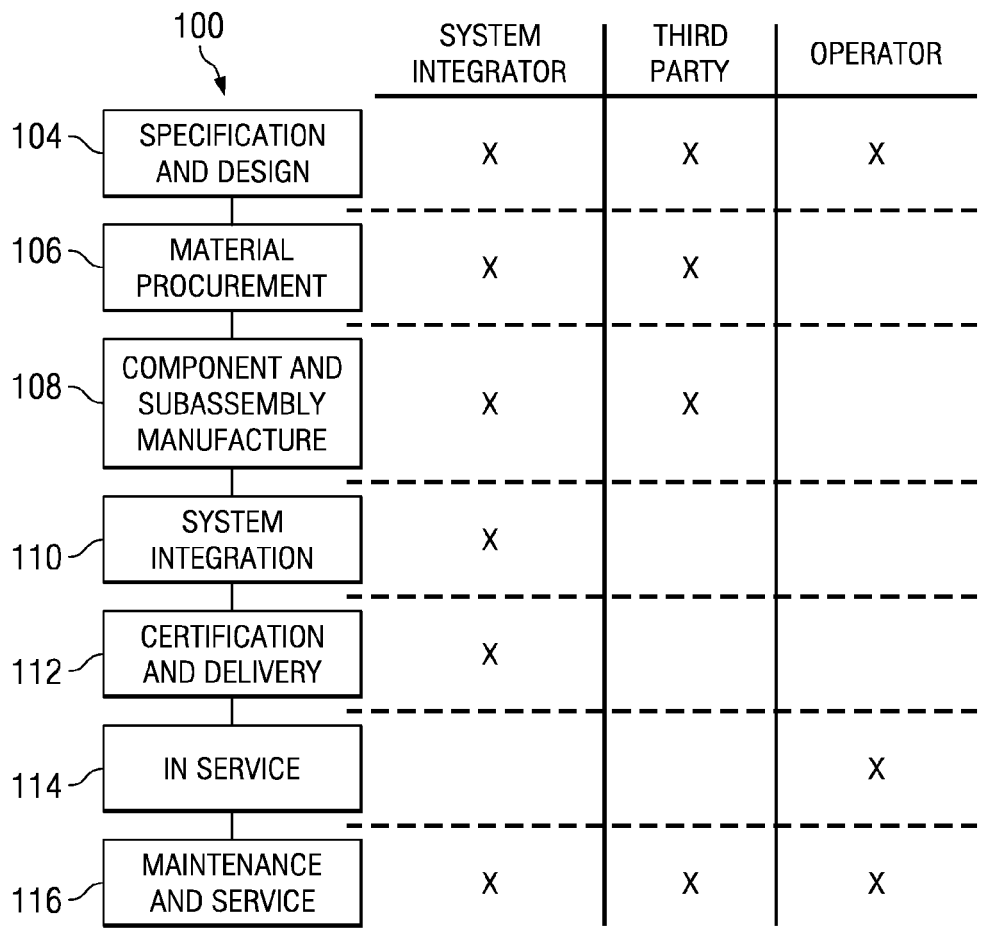
FIG. 1 is a flow diagram of aircraft production and service method in accordance with an advantageous embodiment.
Figure 2:
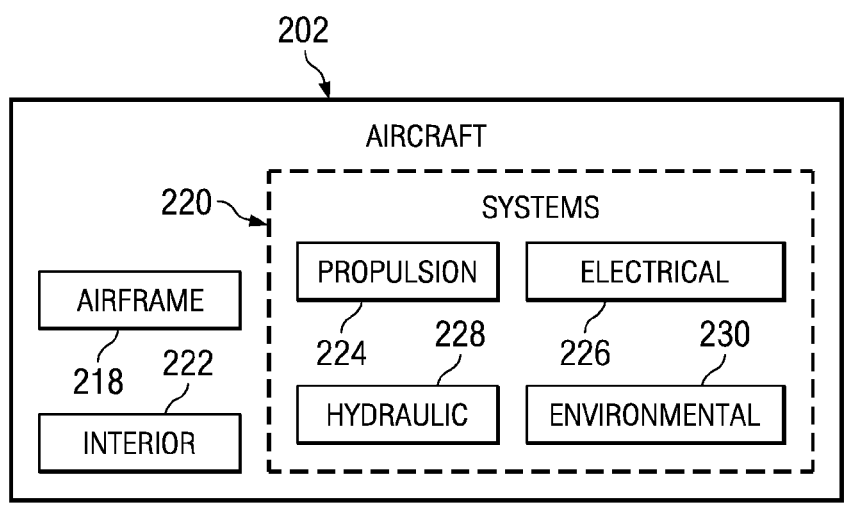
FIG. 2 is a block diagram of an aircraft in accordance with an advantageous embodiment.

Referring more particularly to the drawings, embodiments of the disclosure may be described in the context of an aircraft manufacturing and service method 100 as shown in FIG. 1 and aircraft 202 as shown in FIG. 2. During pre-production, exemplary method 100 may include specification and design 104 of aircraft 202 in FIG. 2 and material procurement 106. During production, component and subassembly manufacturing 108 and system integration 110 of aircraft 202 in FIG. 2 takes place. Thereafter, aircraft 202 in FIG. 2 may go through certification and delivery 112 in order to be placed in service 114. While in service by a customer, aircraft 202 in FIG. 2 is scheduled for routine maintenance and service 116 (which may include modification, reconfiguration, refurbishment, and so on).

Each of the processes of method 100 may be performed or carried out by a system integrator, a third party, and/or an operator (e.g., a customer), as indicated by the "X" in the grid to the right of the flow diagram of FIG. 1. For the purposes of this description, a system integrator may include without limitation any number of aircraft manufacturers and major-system subcontractors; a third party may include without limitation any number of venders, subcontractors, and suppliers; and an operator may be an airline, leasing company, military entity, service organization, and so on.

As shown in FIG. 2, aircraft 202 produced by exemplary method 100 may include airframe 218 with plurality of systems 220 and interior 222. Examples of high-level systems 220 include one or more of propulsion system 224, electrical system 226, hydraulic system 228, and environmental system 230.

Apparatus and methods embodied herein may be employed during any one or more of the stages of production and service method 100 in FIG. 1. For example, components or subassemblies corresponding to production process 108 may be fabricated or manufactured in a manner similar to components or subassemblies produced while aircraft 202 is in service. Also, one or more apparatus embodiments, method embodiments, or a combination thereof may be utilized during production stages 108 and 110 in FIG. 1, for example, by substantially expediting assembly of or reducing the cost of aircraft 202. Similarly, one or more of apparatus embodiments, method embodiments, or a combination thereof may be utilized while aircraft 202 is in service, for example and without limitation, to maintenance and service 116 in FIG. 1.

Many commodities, such as aircraft, may be susceptible to corrosion. These commodities should be inspected and maintained so as to avoid or reduce corrosion on the commodity as much as possible in order for the commodity to function properly and/or efficiently. A commodity is any item that can be manufactured or created for use by a person, company, or other organization. A commodity may include, but is not limited to, any equipment, vehicle, machine, device, or other manufactured item. A commodity may be, for example and without limitation, an airplane, a car, a boat, a helicopter, an engine, a structure, a tool, or any other device or manufactured item having one or more parts and/or surfaces susceptible to corrosion.

As used herein, corrosion refers to a wearing or thinning of a surface thickness, a crack, fracture, or break in surface material, erosion of the surface due to exposure to weather, heat, pressure, an impact, corrosive chemicals, rust, energy, light, an oxidation process, or exposure to any other corrosive substance or corrosive process that results in destruction of a surface material or surface coating.

Therefore, during the manufacture, maintenance, and/or rework of many commodities, such as aircraft, it is extremely important to ensure that external and/or internal surfaces of parts and assemblies associated with the commodity do not have any corrosion. However, corrosion on a surface may be often hidden or masked underneath layers of paint or other surface coatings. Destructive means of corrosion detection require the stripping or removal of paint and/or disassembly of parts and assemblies to identify corrosion. These processes are destructive, slow, inefficient, and may be cost prohibitive.

Conventional nondestructive corrosion detection methods involve visual inspections of surfaces for signs and evidence of corrosion, such as visible rust, dents, cracks, or scratches in the surface without stripping paint or disassembly of parts. However, maintenance personnel and corrosion inspectors must wait until corrosion on a surface is substantial enough to be detected despite paint and other coatings on top of the surface.

The advantageous embodiments recognize that with the increasing use of unitized and complex aerospace structures, there is a critical need for approaches and technologies that allow for non-destructive inspection (NDI) in locations of a structure that are not easily accessible.

Therefore, the advantageous embodiments provide a method, apparatus, and computer usable program code for non-destructive detection of corrosion using quantum dots. In one embodiment, a surface of an area on a commodity associated with a set of quantum dots is tested. A pattern of wavelengths emitted by the set of quantum dots associated with the surface of the commodity is detected to form a quantum dot pattern. The quantum dot pattern is analyzed to determine whether corrosion has occurred in the area on the surface of the commodity.

Figure 3:
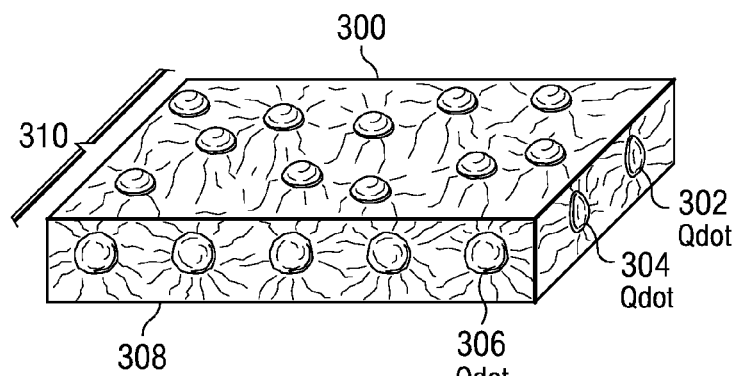
FIG. 3 is an illustration of quantum dots incorporated into a polymer thin film or coating in accordance with an advantageous embodiment.

FIG. 3 is an illustration of quantum dots incorporated into a polymer thin film or coating in accordance with an advantageous embodiment. Quantum dot coating 300 is a coating or substrate having quantum dots, such as quantum dots 302-306 incorporated within the coating or substrate.

Quantum dots 302-306 are particle sized semiconductors that are typically less than 100 nanometers in diameter. In fact, some quantum dots are less than a single nanometer, or one billionth of a meter, in size. Quantum dots 302-306 are tiny crystals, referred to as semiconductor nanocrystals that may consist of a few hundred to a few thousand atoms. Quantum dots 302-306 may be synthesized from a variety of substances, such as, without limitation, silicon, germanium, gallium, arsenide, indium phosphide, cadmium selenide, and zinc sulfide. In this example, quantum dots 302-306 are spherical in shape and made from silicon or other substances.

Quantum dots 302-306 combine the broad absorption spectrum of a semiconductor crystal with the distinct absorption peak of an organic dye, in addition to having longer fluorescent lifetimes. Finally, quantum dots 302-306 can be tuned to emit sharp, Gaussian peaks at any visible, infrared, and ultraviolet frequency.

In this example, quantum dots 302-306 are incorporated into the coating or substrate. In this example, the coating or substrate is, without limitation, polymer coating 308. Quantum dots 302-306 may be implemented as any type of quantum dots. Quantum dots 302-306 may be manufactured using any known or available methods or processes for manufacturing, producing, or generating quantum dots.

In this example, quantum dots 302-306 are imbedded or incorporated into a coating or substrate, such as coating 308 to form quantum dot coating 310. Quantum dots 302-306 are imbedded or incorporated into coating 308 using any known or available method for incorporating quantum dots into a coating or substrate. In other words, any technique known to a person of ordinary skill in the art for generating quantum dot coating 310 may be utilized in accordance with the illustrative embodiments.

In this particular example, coating 308 is a polymer coating. However, the illustrative embodiments may be implemented using quantum dots 302-306 incorporated into any type of substrate or coating. In other words, the embodiments are not limited to incorporating quantum dots 302-306 into a polymer coating.

In this example, quantum dot coating 310 includes approximately eighteen quantum dots. However, this figure is only shown for illustration and not for purposes of limitation. Quantum dot coating 310 may include any number of quantum dots incorporated into a coating to form quantum dot coating 310.

Moreover, the illustrative embodiments are not limited to utilization of quantum dot coating 310. In another embodiment, quantum dots, such as quantum dots 302-306 may be incorporated directly into the material used to manufacture a commodity. In other words, if the commodity is an aluminum panel, quantum dots 302-306 may be imbedded directly within the aluminum of the aluminum panel. Quantum dots can be mixed into a sub-surface coating as well, so when the surface coating breaks down, the quantum dots in the sub-surface coating can be quickly identified.

Colloidally prepared quantum dots are free floating and can be attached to a variety of molecules via metal coordinating functional groups. These groups include, but are not limited to, thiol, amine, nitrile, phosphine, phosphine oxide, phosphonic acid, carboxylic acid, or other ligands. This ability to attach to other molecules greatly increases the flexibility of quantum dots with respect to the types of environments in which they can be applied. By bonding appropriate molecules to the surface of a commodity, the quantum dots can be dispersed or dissolved in nearly any solvent or incorporated into a variety of inorganic and organic films. In addition, the surface chemistry can be used to effectively alter the properties of the quantum dots, including the brightness and electronic lifetimes of the quantum dots.

Figure 4:
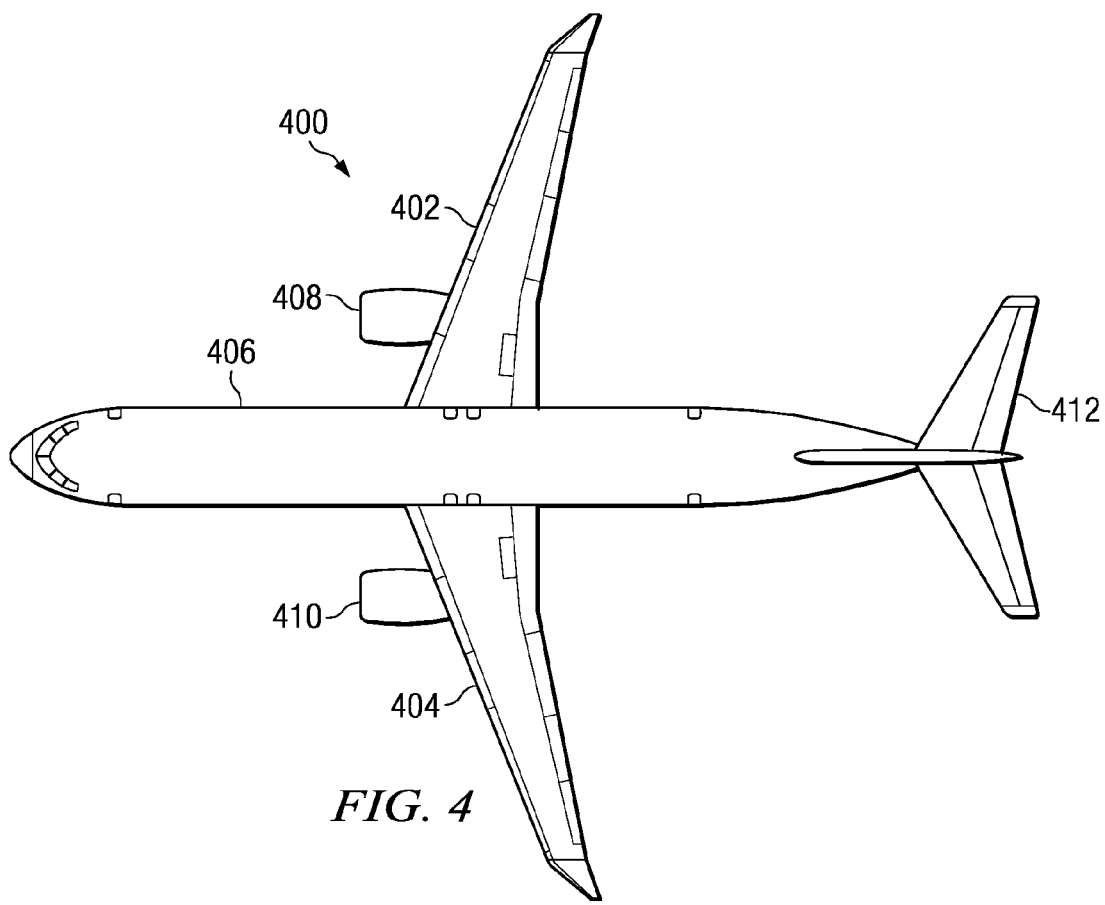
FIG. 4 is an illustration of an airplane having quantum dots associated with a surface of the airplane for use in detecting corrosion on the surface in accordance with an advantageous embodiment.

With reference now to FIG. 4, an illustration of an airplane having quantum dots associated with a surface of the airplane for use in detecting corrosion on the surface is shown in accordance with an advantageous embodiment. Airplane 400 is an example of an aircraft in which quantum dots have been associated with one or more surfaces of airplane 400 for enhancing detection of corrosion. In this illustrative example, airplane 400 has wings 402 and 404 attached to body 406. Airplane 400 includes wing mounted engine 408, wing mounted engine 410, and tail 412.

Airplane 400 may be any type of known or available aircraft or aerospace vehicle, such as, without limitation, aircraft 202 in FIG. 2. Airplane 400 includes quantum dots associated with a set of one or more surfaces on airplane 400. A surface may be an external surface or an internal surface of a commodity.

Airplane 400 is an example of a commodity. However, the illustrative embodiments are not limited to implementation in association with an aircraft. The illustrative embodiments may also be implemented with any type of commodity, including, but not limited to, cars, trucks, vans, helicopters, boats, ships, ocean going vessels, non-mobile structures, and/or any other type of commodity.

In addition, the illustrative embodiments may be used to detect corrosion on parts or assemblies for a commodity. For example, the illustrative embodiments may be used to detect corrosion on a wing assembly designed for use on airplane 400 even if the wing assembly is not attached to airplane 400. In other words, the process described in FIGS. 4-9 below may be utilized in conjunction with a fully assembled commodity, such as an airplane, or in conjunction with any part or assembly for a commodity, such as a wing assembly, a fuselage, a door, a propeller blade, or any other piece or part of a commodity. Other example, parts, assemblies, or sub assemblies may be for other types of vehicles or structures other than an aircraft, such as airplane 400. For example, quantum dots may be associated with a surface of a blade in a steam turbine generator or with a surface of a pipe for a power plant.

Figure 5:
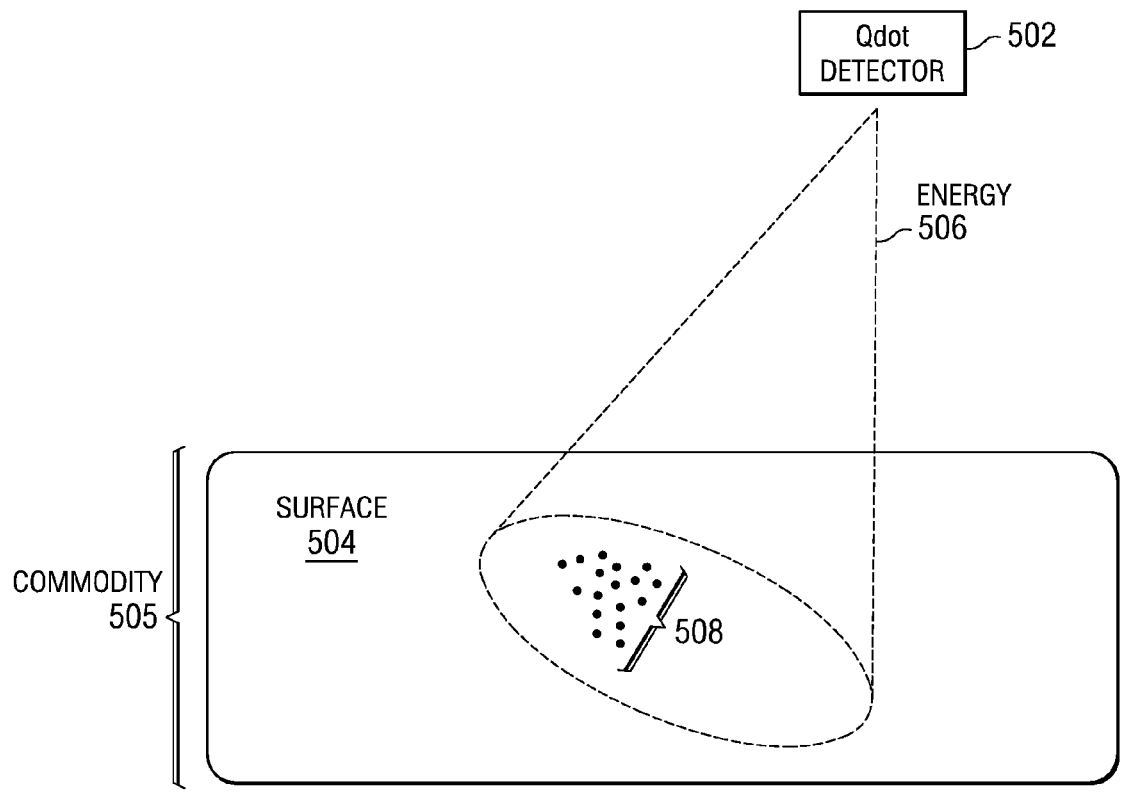
FIG. 5 is an illustration of a corrosion detection system in accordance with an advantageous embodiment.

Referring now to FIG. 5, an illustration of a corrosion detection system is shown in accordance with an advantageous embodiment. A corrosion detection system is a system for nondestructive corrosion detection using quantum dots associated with a surface and/or area of a commodity.

In this example, the corrosion detection system uses set of quantum dots 508 associated with surface 504 of commodity 505 to detect corrosion. Commodity 505 may be any type of commodity. In this example and without limitation, commodity 505 may be a piece or part of an aluminum wing of an aircraft, such as airplane 400 in FIG. 4.

In one embodiment, quantum dots are associated with surface 504 of commodity 505 by placing quantum dots within the material comprising the commodity. In this example, the quantum dots are mixed into the metal structure of commodity 505 during manufacture.

In another embodiment, quantum dots are associated with surface 504 by imbedding or integrating quantum dots in a coating that is applied to surface 504 to cover commodity 505. In other words, quantum dots are placed within the material of commodity 505 or applied in a coating or substrate to surface 504 of commodity 505 to act as a marker for corrosion detection. The quantum dots are released as the material making up commodity 505 corrodes.

The quantum dots can be easily and rapidly identified using quantum dot (Q-dot) detector 502. Q-dot detector 502 is a device for detecting a presence of quantum dots in a structure, such as commodity 505, or in a coating on surface 504 of commodity 505. Q-dot detector 502 may be a device that is adjusted or calibrated to be sensitive to the range of florescent excitation emitted by the quantum dots associated with surface 504.

For example, Q-dot detector 502 may be, but is not limited to, an optical device for detecting visible, infrared, and ultraviolet wavelengths of light, a borescope that is designed for sensitivity to wavelengths of light in the appropriate range, spectroscopy device, a photo-spectroscopy device, a combination of a borescope and an optical device, or any other device known or available in the art for detecting wavelengths of light or signals emitted by quantum dots.

A combination of a borescope and an optical device would provide a hybrid Q-dot detector that is capable of detecting Q-dot patterns in inaccessible areas or remote areas. Thus, this embodiment would increase the speed and efficiency of corrosion testing.

In another embodiment, Q-dot detector 502 may be, without limitation, a pair of goggles worn by a human user that enables the human user to see ultraviolet light and/or infrared light, in addition to the normal visual spectrum of light.

Figure 6:
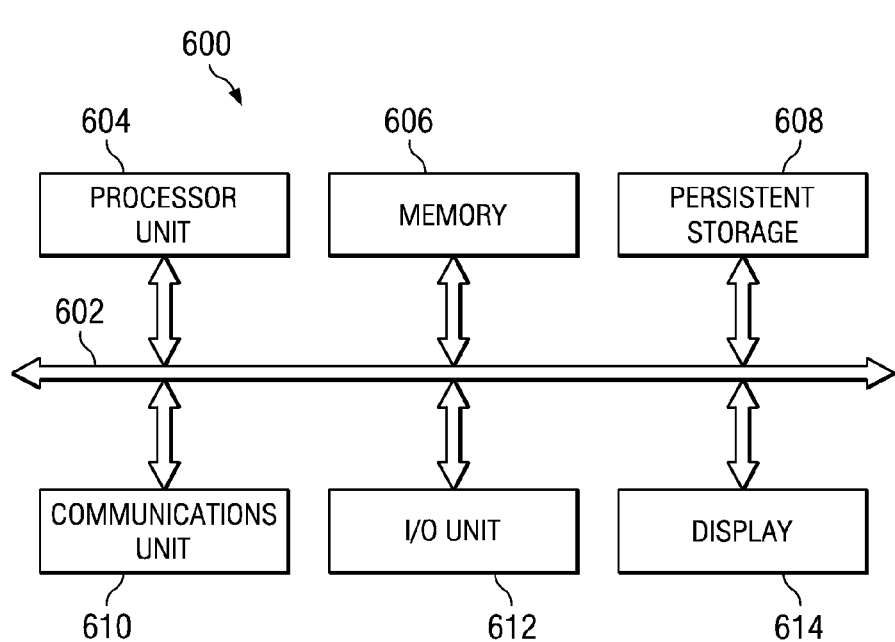
FIG. 6 is an illustration of a data processing system in accordance with an advantageous embodiment.

Q-dot detector 502 may optionally include a computing device, such as, without limitation, a processor and a memory, for processing data regarding emissions by the quantum dots gathered by Q-dot detector 502, such as is shown in FIG. 6 below. Q-dot detector 502 may also optionally include a network device for transmitting data, such as data regarding wavelengths of energy emitted by quantum dots, over a network to a remote computing device for processing.

Data regarding the wavelengths of light emitted by the quantum dots and the intensity of the wavelengths of the light may be processed by Q-dot detector 502 and/or by any other type of computing device, to determine the type and amount of corrosion on surface 504. In other words, the data can be processed to determine the exact location of the corrosion, the severity of the corrosion, how far or deeply the corrosion has progressed, and the nature of the corrosion. For example, an analysis of the quantum dot signals may reveal that the corrosion is superficial or has not reached beneath a particular layer of surface 504, the exact areas of surface 504 experiencing corrosion, and/or that the corrosion is likely due to rust.

Quantum dots are tiny crystals with sizes on the order of nanometers. Electrons within a quantum dot can absorb energy 506, such as, without limitation, electricity, sunlight, heat, microwaves, or electromagnetic radiation, and emit energy as light or a current in response. In this example, an area on surface 504 associated with the set of quantum dots is tested for corrosion when Qdot detector 502 applies or emits energy 506 to the area on surface 504 of commodity 505 to excite set of quantum dots 508 associated with surface 504. When set of quantum dots 508 are exited, they emit energy in the form of wavelengths of light. However, in accordance with the illustrative embodiments, any type of energy may be applied to the area on surface 504 to excite the set of quantum dots. In other words, the embodiments are not limited to application of energy 506 to excite the set of quantum dots.

In this example, energy 506 is a specific wavelength of electromagnetic radiation for exciting quantum dots associated with commodity 505. However, energy 506 may also be implemented using, without limitation, heat, microwaves, or electricity to excite the quantum dots.

Exciting the quantum dots causes the quantum dots to fluoresce or emit visible light, ultraviolet, and/or infrared light. The light emitted by the quantum dots may vary in wavelength and color. For example, one quantum dot may emit visible blue light when excited and another quantum dot may emit visible red light when excited.

In other words, the wavelength of light emitted from a quantum dot is related to its size. Thus, quantum dots are tunable, such that the signals or wavelengths emitted by a quantum dot can be selected or adjusted by changing the size of the quantum dot and/or changing the chemical composition of the quantum dot. In other words, the emission wavelength, and consequently the color of light emitted by the quantum dot, can be altered simply by changing the size of the quantum dot. Smaller quantum dots yield smaller or shorter wavelengths that tend to fall more within the blue color range of light. Larger quantum dots emit longer wavelengths of light which produces a red colored light emission. Quantum dots of different sizes can be tethered or linked together to form molecules, attached to a polymer backbone, linked or tethered to form chains, and/or linked to form lattices. Each quantum dot in these chains and lattices that are of differing size will emit different wavelengths of light. In this manner, different sized quantum dots can be linked together to form lattices of quantum dots that will emit different colored lights in different patterns.

If multiple sized quantum dots are mixed together and then linked, a specific identifiable code pattern on the substrate or surface 504 is formed, which may be multicolored and can be identified by its unique quantum dot pattern, similar to a bar code. Thus, a quantum dot barcode with specific fluoroscopic characteristics may be selectively or uniformly embedded into the material used to manufacture a commodity or into a coating or substrate used to coat or cover the commodity after manufacture of the commodity, as discussed above in FIG. 3.

The pattern of different wavelengths emitted when the quantum dots are excited forms quantum dot (Q-dot) pattern 508. Q-dot pattern 508 is the pattern of wavelengths of visible, infrared, and ultraviolet light emitted by quantum dots in an area of surface 504 on commodity 505 that are excited by energy 506. Q-dot detector 502 detects the wavelengths emitted by the quantum dots and processes data associated with the wavelengths to form Q-dot pattern 508. Q-dot pattern 508 may be used as an indicator if subsequent damage to the part or area of commodity 505 occurs. For instance, once the alloy in an area begins to corrode, the quantum dots associated with that area will break loose from the alloy crystals and surface during oxidation. Q-dot detector 502 can then detect and highlight the particular signature emitted by the quantum dots to form Q-dot pattern 508.

Q-dot detector 502 then outputs to a user Q-dot pattern 508 and/or additional data regarding corrosion associated with the area on surface 504 being checked for corrosion. For example, the additional data may include data such as the severity or extent of the corrosion, the location of the corrosion, and/or instructions for further testing of the area to confirm corrosion. Q-dot detector 502 may be necessary to detect wavelengths of light emitted by the quantum dots that are not visible to the human eye. In addition, Q-dot detector 502 is capable of measuring the intensity of the wavelength signals emitted by the quantum dots more accurately then a human user.

In this illustrative embodiment, if commodity 505 is an airplane wing made of aluminum alloy, the quantum dots may be selectively embedded into the aluminum alloy of the airplane wing itself during manufacture or fabrication of the wing. Once the alloy or surface of the commodity begins to corrode, the quantum dots will break loose from the alloy crystals and surfaces during oxidation. Q-dot detector 502 detects and highlights the particular signature from the quantum dots to generate Q-dot pattern 508. Q-dot pattern 508 may vary depending on the size, number, and linkages between the quantum dots associated with surface 504.

In this embodiment, quantum dots are associated with surface 504 in a pattern for nano-barcoding of the aluminum making up surface 504 of commodity 505, as part of the overall corrosion detection system 500. However, quantum dots may also be associated with the surface without a pattern or nano-barcoding. In this embodiment, quantum dots of uniform size are applied evenly over the surface of the commodity or distributed evenly throughout the material used to manufacture the commodity.

In another embodiment, quantum dots may be integrated directly into a resin in a composite during curing. If an area on commodity 505 including the composite develops micro-cracking, particulates will begin to release into ambient air. In other words, the micro-cracking allows the particulates in the composite to break free from the remaining composite at the area of the micro-cracking. Q-dot detector 502 can then detect Q-dot pattern 508 emitted by the quantum dots. In this example, Q-dot detector 502 may be a set of one or more fluorescent probes.

In another embodiment, one or more Q-dot detectors, such as Q-dot detector 502 may be a part of a networked structural health management system. In this embodiment, Q-dot detectors placed at various locations on a structure, such as commodity 505, are periodically and/or automatically interrogated by a computer system to determine whether damage or corrosion has occurred and/or receive an indication of corrosion or damage that has occurred.

For example, a set of two or more Q-dot detectors may be placed at equal or irregular intervals on a surface of commodity 505 or placed throughout commodity 505. A computer system, such as the data processing system depicted in FIG. 6 below, interrogates the Q-dot detectors to determine whether corrosion has occurred. When the interrogation signal is received by the set of Q-dot detectors, the Q-dot detectors release energy to excite Q-dots located within a range of each Q-dot detector in the set of Q-dot detectors. A determination may then be made as to whether corrosion has occurred based on the pattern and intensity of wavelengths emitted by the Q-dots located within range of the Q-dot detectors.

Turning now to FIG. 6, a diagram of a data processing system is depicted in accordance with an illustrative embodiment of the disclosure. In this illustrative example, data processing system 600 is a data processing system incorporated within a quantum dot detector, such as Q-dot detector 502 in FIG. 5. However, data processing system 600 may also be a remote computing device to Q-dot detector 502 in FIG. 5 that receives data regarding the amount, pattern, intensity, wavelength, and any other information regarding emissions from quantum dots associated with a surface of a commodity.

Data processing system 600 includes bus 602, which provides communications between processor unit 604, memory 606, persistent storage 608, communications unit 610, input/output (I/O) unit 612, and display 614.

Processor unit 604 serves to execute instructions for software that may be loaded into memory 606. Processor unit 604 may be a set of one or more processors or may be a multi-processor core, depending on the particular implementation. Further, processor unit 604 may be implemented using one or more heterogeneous processor systems in which a main processor is present with secondary processors on a single chip. Memory 606, in these examples, may be, for example, a random access memory. Persistent storage 608 may take various forms depending on the particular implementation. For example and without limitation, persistent storage 608 may be a hard drive, a flash memory, a rewritable optical disk, a rewritable magnetic tape, or some combination of the above.

Communications unit 610, in these examples, provides for communications with other data processing systems or devices. In these examples, communications unit 610 is a network interface card. I/O unit 612 allows for input and output of data with other devices that may be connected to data processing system 600. For example, I/O unit 612 may provide a connection for user input through a keyboard and mouse. Further, I/O unit 612 may send output to a printer. Display 614 provides a mechanism to display information to a user.

Instructions for the operating system and applications or programs are located on persistent storage 608. These instructions may be loaded into memory 606 for execution by processor unit 604. The processes of the different embodiments may be performed by processor unit 604 using computer implemented instructions, which may be located in a memory, such as memory 606.

Figure 7:
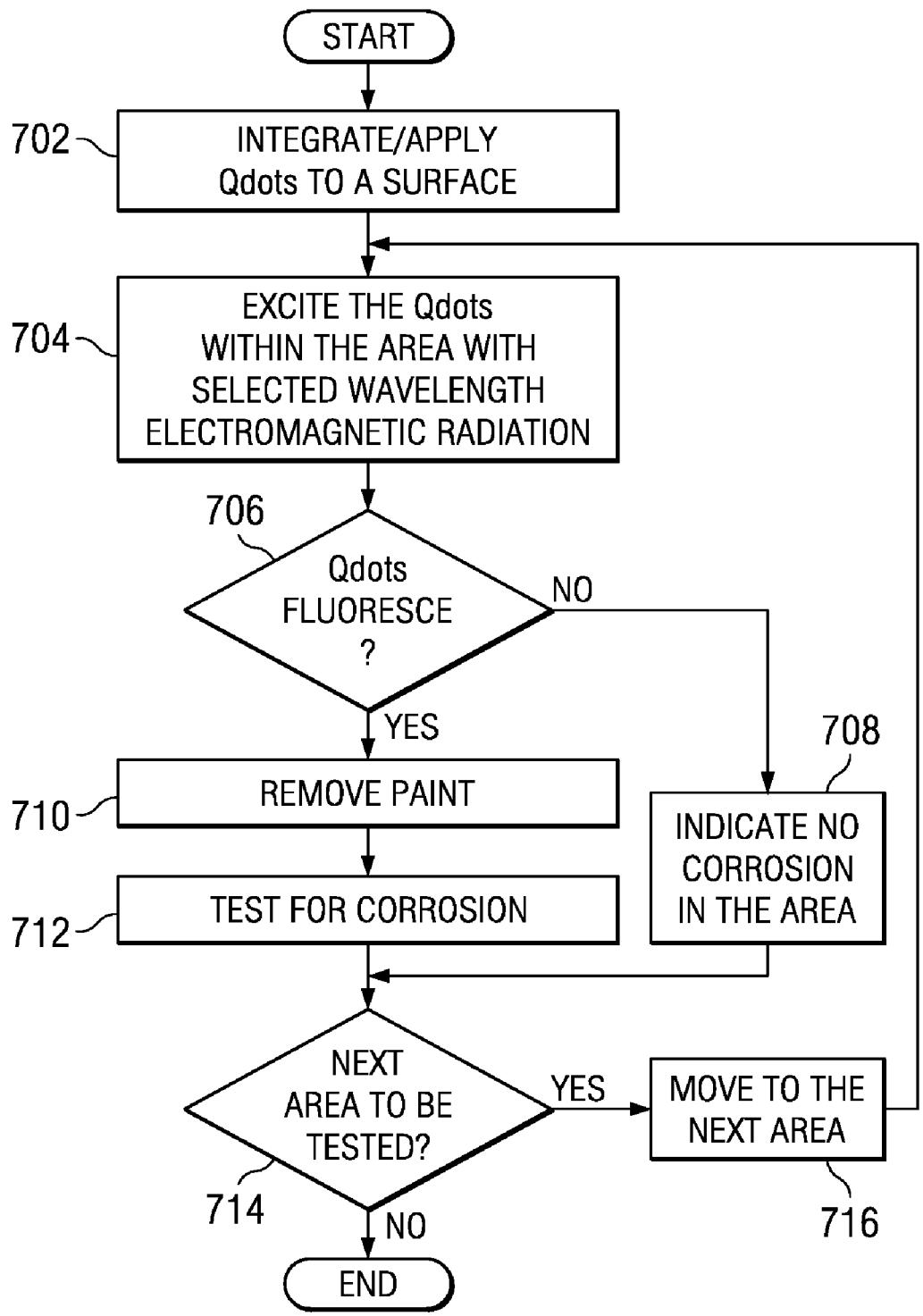
FIG. 7 is a flowchart of a process for nondestructive corrosion detection using quantum dots associated with a surface of a commodity in accordance with an advantageous embodiment.

Turning now to FIG. 7, a flowchart of a process for nondestructive corrosion detection using quantum dots associated with a surface of a commodity is shown in accordance with an advantageous embodiment. The process may be implemented by maintenance personnel or one or more other humans.

The process begins by integrating quantum dots into a material of a commodity, such as airplane 400 in FIG. 4 or commodity 505 in FIG. 5 or applying a coating or substrate including the quantum dots to a surface of the commodity (operation 702). The quantum dots are excited within an area on the surface of the commodity using a selected wavelength of electromagnetic radiation (operation 704). A determination is made as to whether the quantum dots fluoresce in a manner or pattern that indicates corrosion (step 706). If the quantum dots do not fluoresce in a manner or pattern that indicates corrosion, it indicates that there is no corrosion in the area (operation 708).

Returning to operation 706, if the quantum dots fluoresce in a pattern or in a manner that indicates corrosion, the paint covering the area is removed (operation 710) and a test for corrosion is performed (operation 712).

After testing the area for corrosion in operation 712 or if there is no corrosion indicated in the area at operation 708, a determination is made as to whether a next area needs to be checked for corrosion (operation 714). If a next area needs to be checked, the process moves to the next area to be tested (step 716). The process then returns to step 704 and continues implementing operations 704-714 until all areas that need to be checked have been checked for corrosion. When a determination is made that a next area does not need to be checked at operation 714, the process terminates thereafter.

Figure 8:
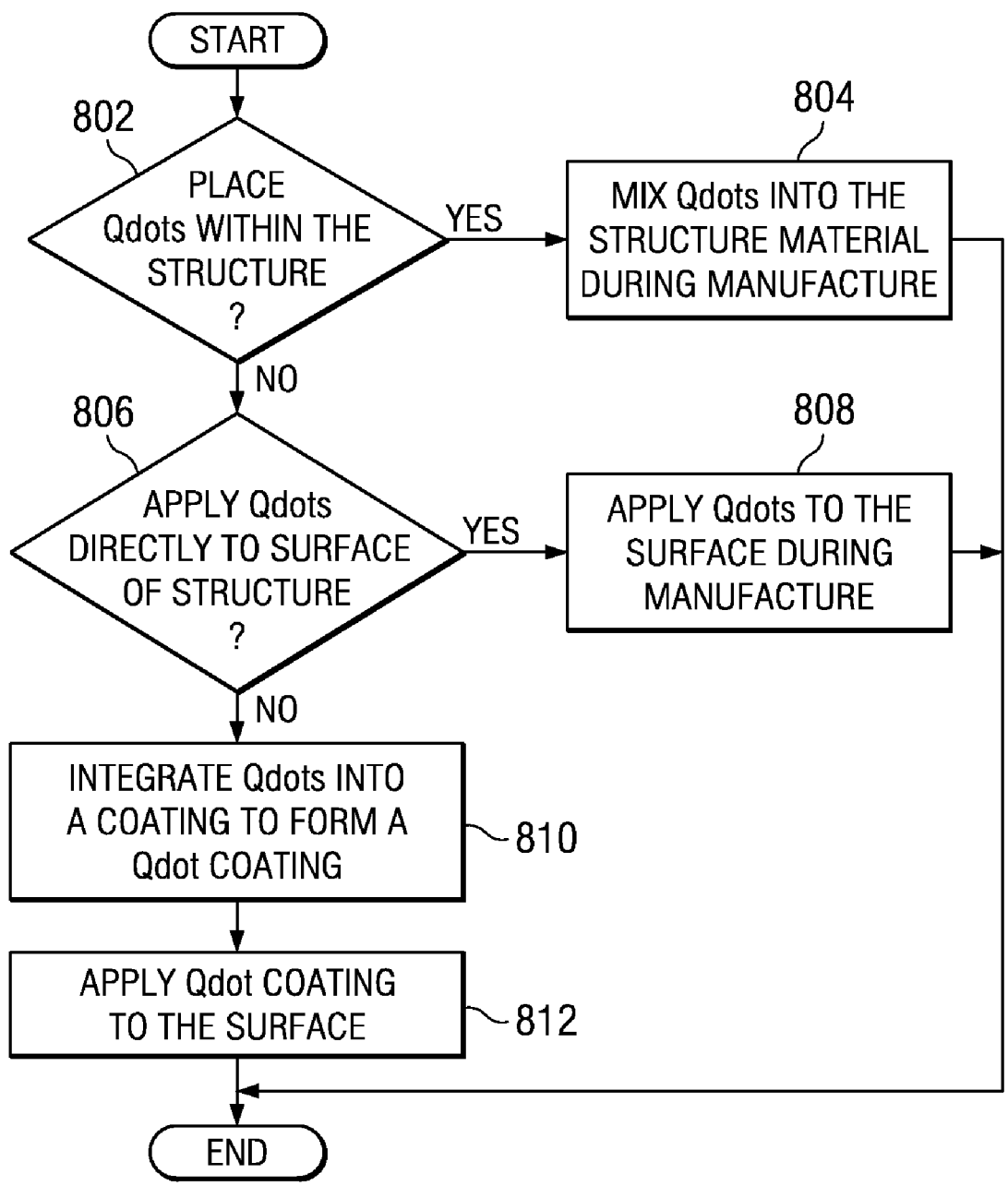
FIG. 8 is a flowchart of a process for associating quantum dots with a surface of a commodity in accordance with an advantageous embodiment.

FIG. 8 is a flowchart of a process for associating quantum dots with a surface of a commodity in accordance with an advantageous embodiment. The process may be implemented by manufacturers, maintenance personnel, or one or more other humans. The process in FIG. 8 is a more detailed implementation of step 502 in FIG. 5.

The process begins by making a determination as to whether to place quantum dots within the structure or material making up a part or area of the commodity (operation 802). If quantum dots are to be placed inside or into the material or structure of the commodity, quantum dots are mixed directly into the structure material of the commodity (operation 804) with the process terminating thereafter. In this operation, quantum dots may be integrated directly into a resin in a composite during curing.

Returning to operation 802, if quantum dots are not placed within the structure or material comprising the commodity, a determination is made as to whether the quantum dots should be applied in a substrate directly to the surface of the commodity (operation 806). If quantum dots are to be applied directly to the surface, the quantum dots are added to a substrate and applied directly to the surface of the commodity (operation 808). This operation may be performed during manufacture or after manufacture, such as during maintenance of the commodity.

Returning to operation 806, if the quantum dots are not to be applied to the surface in a substrate, the quantum dots are integrated into a coating to form a quantum dot coating (operation 810). The quantum dot coating is applied to the surface of the commodity (operation 812) with the process terminating thereafter.

Figure 9:
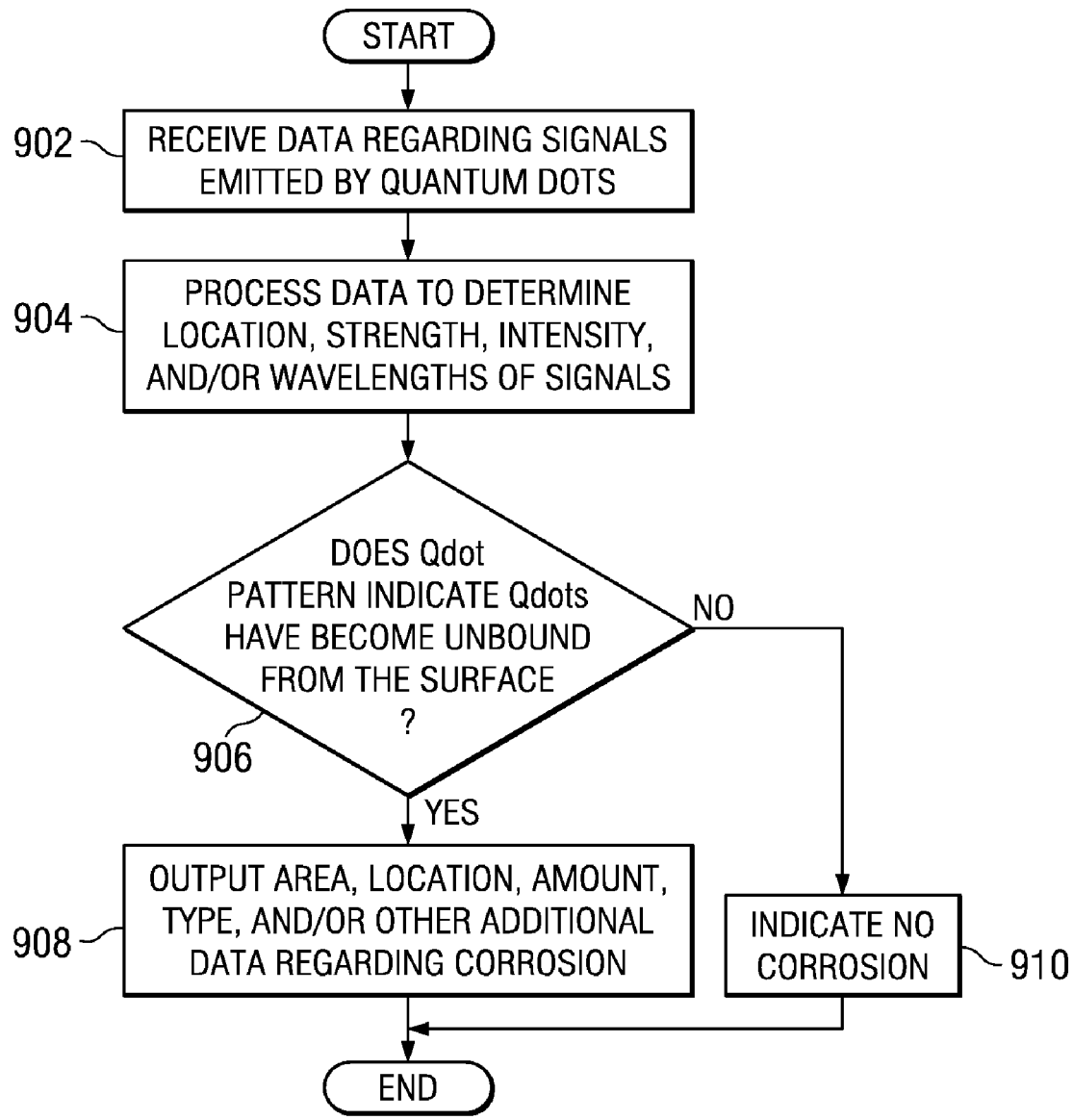
FIG. 9 is a flowchart of a process for processing quantum dot signals to identify corrosion in accordance with an advantageous embodiment.

FIG. 9 is a flowchart of a process for processing quantum dot signals to identify corrosion in accordance with an advantageous embodiment. The process in FIG. 9 may be implemented in any type of computing device, such as by Q-dot detector 502 in FIG. 5 or data processing system 600 in FIG. 6. The process in FIG. 9 may be a part of a networked structural health management system, where detectors are periodically and/or automatically interrogated by a computer system.

The process begins by receiving data regarding signals emitted by quantum dots associated with a surface of a commodity (operation 902). In this example, the term "signals" refers to the energy or wavelengths of visible light, ultraviolet light, and/or infrared light emitted by one or more quantum dots.

The Q-dot detector processes the data to determine the location, strength, intensity, wavelengths, and/or any other additional data regarding the signals (operation 904).

The Q-dot detector makes a determination as to whether the code pattern has become unbound from the surface due to corrosion (operation 906). In other words, the quantum dots associated with the surface of the commodity should emit a particular Q-dot pattern in the absence of corrosion. A change in the expected pattern may indicate corrosion of the surface that has caused the quantum dots to become unbound during an oxidation process or other corrosion process.

If the Q-dot pattern indicates corrosion, the Q-dot detector outputs the area or location of the corrosion, the amount or severity of the corrosion, the type of corrosion, and/or any other data or conclusions regarding the corrosion (operation 908) with the process terminating thereafter.

Returning to operation 906, if the Q-dot pattern does not indicate corrosion, the Q-dot detector indicates no corrosion (operation 910) with the process terminating thereafter. An indication of no corrosion may be made in a variety of ways, including, but not limited to, a signal, icon, a text message, a verbal message, or by any other means of indicating a lack of corrosion.

In this example, the data is processed in step 904 by the Q-dot detector. However, in another embodiment, the Q-dot detector transmits the data regarding signals emitted by quantum dots over a network to a remote computing device. The remote computing device processes the data to determine location, strength, and/or wavelengths of signals. The remote computing device may then send the results of processing the data to a display device for display to a user, to a data storage device for storage of the results, and/or transmit the results back to the Q-dot detector.

Also, in this example, a single Q-dot detector is used to excite quantum dots associated with a commodity. However, in another example, a set of two or more Q-dot detectors may be used to excite quantum dots associated with the commodity.

Thus, the advantageous embodiments provide a method, apparatus, and computer usable program code for non-destructive detection of corrosion using quantum dots. In one embodiment, a surface of an area on a commodity associated with a set of quantum dots is tested. A pattern of wavelengths emitted by the set of quantum dots associated with the surface of the commodity is detected to form a quantum dot pattern. The quantum dot pattern is analyzed to determine whether corrosion has occurred in the area on the surface of the commodity.

Thus, the illustrative embodiments provide a quantum dot based system for early, nondestructive detection of corrosion. Quantum dot "bar codes" are placed either within a structure or on a structure substrate to act as a marker for corrosion that can be easily and rapidly identified and quantified by measurement devices, such as a quantum dot detector. The quantum dots may be mixed directly into the structure during manufacture, applied to the surface of the structure, and/or integrated into a coating that covers the structure.

The utilization of quantum dots to enhance visual inspections to detect corrosion in accordance with the illustrative embodiments reduces inspection and maintenance cycle costs for aircraft subject to corrosion. For example, corrosion can be detected in a non-destructive manner without stripping or removing paint from surfaces. The illustrative embodiments also provide improved sensitivity to corrosion and detect corrosion that might otherwise go undetected using conventional methods, permit remote detection of corrosion, and improve corrosion detection speed and efficiency.

The utilization of quantum dots in the illustrative embodiments also allow a more rapid corrosion inspection with more accurate results, more extended maintenance intervals between corrosion inspections, and less disassembly during inspections. These benefits and advantages of the illustrative embodiments can significantly reduce the cost of maintaining aircraft and other commodities.

Quantum dots and nano technology can also be integrated at the atomic level into many products in the aerospace industry, and other manufacturing, inspection, maintenance, and rework processes in accordance with the illustrative embodiments to improve inspection and maintenance cycle costs. For example, the embodiments may be used to detect corrosion in automobiles, boats, in piping, and in any other area where corrosion detection may be beneficial.

The flowchart and block diagrams in the figures illustrate the architecture, functionality, and operation of possible implementations of systems, methods and computer program products according to various embodiments. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved.

The description of the embodiments has been presented for purposes of illustration and description, and is not intended to be exhaustive or limited to the invention in the form disclosed. Many modifications and variations will be apparent to those of ordinary skill in the art. Further, different advantageous embodiments may provide different advantages as compared to other advantageous embodiments. The embodiment or embodiments selected are chosen and described in order to best explain the principles of the invention, the practical application, and to enable others of ordinary skill in the art to understand the invention for various embodiments with various modifications as are suited to the particular use contemplated.

What is claimed is:

1. A method for non-destructive detection of corrosion using quantum dots, the method comprising:
    testing, by a number of quantum dot detectors operably coupled to a data processing system, a surface on a commodity associated with a set of quantum dots to form a test area;
    detecting, by a processor of the data processing system, a pattern of wavelengths emitted by the set of quantum dots associated with the test area of the commodity to form a quantum dot pattern, wherein the set of quantum dots emits different colored lights in different sets of patterns of wavelengths;
    identifying, by the processor, an intensity of wavelengths in the pattern of wavelengths emitted by the set of quantum dots;
    analyzing, by the processor, the quantum dot pattern to determine whether corrosion has occurred in the test area, wherein the set of quantum dots emit an expected pattern in the absence of corrosion, and wherein the corrosion changes the expected pattern; and
    determining, by the processor, an amount and a severity of corrosion in the test area of the commodity based on the quantum dot pattern and the intensity of the wavelengths.

2. The method of claim 1 further comprising:
    incorporating the set of quantum dots into a material used to synthesize the test area of the commodity during manufacture of the commodity.

3. The method of claim 1 further comprising:
    incorporating the set of quantum dots within a coating used to cover the surface of the test area of the commodity.

4. The method of claim 1 further comprising:
applying the set of quantum dots directly to the test area of the commodity.

5. The method of claim 1 wherein testing the surface on the commodity further comprises:
exciting, by the number of quantum dot detectors, the set of quantum dots in the test area using energy, wherein exciting the set of quantum dots causes the quantum dots to emit the pattern of the wavelengths.

6. The method of claim 1 wherein the commodity is an aircraft.

7. The method of claim 1 wherein analyzing the quantum dot pattern to determine whether corrosion has occurred in the test area of the commodity further comprises:
receiving, by the processor, data describing the quantum dot pattern emitted by the set of quantum dots;
processing, by the processor, the data to determine whether the quantum dot pattern indicates corrosion; and
responsive to an indication of corrosion, identifying, by the processor, a strength of the wavelengths in the pattern of wavelengths to identify the amount and the severity of the corrosion.

8. The method of claim 1 wherein detecting the pattern of wavelengths emitted by the set of quantum dots associated with the surface of the commodity to form the quantum dot pattern further comprises:
determining, by the processor, a location and a strength of a wavelength emitted by each quantum dot in the set of quantum dots to form the quantum dot pattern.

9. A computer program product comprising:
a non-transitory computer readable medium containing computer usable program code for non-destructive detection of corrosion using quantum dots, said computer program product comprising:
computer usable program code for detecting a pattern of wavelengths emitted by a set of quantum dots associated with the surface of the commodity to form a quantum dot pattern in response to a test of a surface of a commodity associated with a set of quantum dots to form a test area, wherein the set of quantum dots emits different colored lights in different sets of patterns of wavelengths;
computer usable program code for identifying an intensity of wavelengths in the pattern of wavelengths emitted by the set of quantum dots;
computer usable program code for analyzing the quantum dot pattern to determine whether corrosion has occurred in the test area of the commodity, wherein the set of quantum dots emit an expected pattern in the absence of corrosion, and wherein the corrosion changes the expected pattern; and
computer usable program code for determining an amount and a severity of corrosion in the test area of the commodity based on the quantum dot pattern and the intensity of the wavelengths.

10. The computer program product of claim 9 further comprising:
computer usable program code for receiving data describing the quantum dot pattern emitted by the set of quantum dots;
computer usable program code for processing the data to determine whether the quantum dot pattern indicates corrosion in the test area; and
computer usable program code for identifying a strength of wavelengths in the pattern of wavelengths to identify an amount of corrosion in response to an indication of corrosion.

11. The computer program product of claim 10 further comprising:
computer usable program code for receiving the data describing the quantum dot pattern emitted by the set of quantum dots from a quantum dot detector.

12. The computer program product of claim 9 wherein the set of quantum dots is incorporated into a material used to synthesize the test area of the commodity during manufacture of the commodity.

13. The computer program product of claim 9 wherein the set of quantum dots is incorporated within a coating used to cover the surface of the test area of the commodity.

14. A system for non-destructive detection of corrosion using quantum dots, the system comprising:
a commodity;
a set of quantum dots associated with an area of the commodity to form a test area; and
a quantum dot detector, wherein the quantum dot detector detects a pattern of wavelengths emitted by the set of quantum dots associated with the test area of the commodity to form a quantum dot pattern, wherein the set of quantum dots emits different colored lights in different sets of patterns of wavelengths; identifies an intensity of wavelengths in the pattern of wavelengths emitted by the set of quantum dots; analyzes the quantum dot pattern to determine whether corrosion has occurred in the test area of the commodity, wherein the set of quantum dots emit an expected pattern in the absence of corrosion, and wherein the corrosion changes the expected pattern; and determines an amount and a severity of corrosion in the test area of the commodity based on the quantum dot pattern and the intensity of the wavelengths.

15. The system of claim 14 wherein the set of quantum dots is incorporated into a material used to synthesize the test area of the commodity during manufacture of the commodity.

16. The system of claim 14 further comprising:
a coating on the surface of the test area of the commodity, wherein the set of quantum dots are incorporated within the coating.

17. The system of claim 14 further comprising:
a set of quantum dot detectors associated with the commodity, wherein the set of quantum dot detectors detect the pattern of wavelengths emitted by the set of quantum dots within a range of the set of quantum dot detectors to form a set of quantum dot patterns and analyze the set of quantum dot patterns to determine whether corrosion has occurred within the range of the set of quantum dot detectors.

* * * * *